United States Patent [19]

Mino et al.

[11] Patent Number: 5,461,166
[45] Date of Patent: Oct. 24, 1995

[54] CHEMICALLY ADSORBED ULTRATHIN FILM AND ITS MATERIAL, AND METHOD OF MANUFACTURING THE SAME

[75] Inventors: Norihisa Mino, Settsu; Kazufumi Ogawa, Nara; Toshinobu Ishihara, Joetsu; Mikio Endo, Joetsu; Tohru Kubota, Joetsu; Kazuyuki Asakura, Joetsu, all of Japan

[73] Assignee: Matsushita Electric Industrial Co., Ltd., Osaka, Japan

[21] Appl. No.: 384,594

[22] Filed: Feb. 3, 1995

Related U.S. Application Data

[63] Continuation of Ser. No. 107,004, Aug. 17, 1993, abandoned.

[30] Foreign Application Priority Data

Sep. 10, 1992  [JP]  Japan .................................. 4-242352

[51] Int. Cl.⁶ ..................... C07D 333/02; C08G 77/08; C08F 28/06
[52] U.S. Cl. ................. 549/4; 549/214; 528/15; 528/30; 528/31; 528/32; 526/256
[58] Field of Search .................. 549/4, 214; 528/30, 528/380, 15, 31, 32; 526/256

[56] References Cited

U.S. PATENT DOCUMENTS

| | | | |
|---|---|---|---|
| 2,640,818 | 6/1953 | DiGiorgio | 549/4 |
| 4,049,676 | 9/1977 | Schilling, Jr. | 549/4 |
| 4,208,342 | 6/1980 | Bargain et al. | 549/4 |
| 5,214,176 | 5/1993 | Soula et al. | 549/4 |
| 5,223,331 | 6/1993 | Ogawa et al. | 428/209 |

FOREIGN PATENT DOCUMENTS

| | | |
|---|---|---|
| 0445534 | 9/1991 | European Pat. Off. |
| 0540839 | 5/1993 | European Pat. Off. |
| 3076714 | 4/1991 | Japan . |

OTHER PUBLICATIONS

Tetrahedron, vol. 38, No. 22, 1982, pp. 3347–3354, K. Tamao et al., "Nickel–Phosphine Complex–Catalyzed Grignard Coupling–II; Grignard Coupling OH Heterocyclic Compounds".

*Primary Examiner*—Richard L. Raymond
*Assistant Examiner*—Deborah Lambkin
*Attorney, Agent, or Firm*—Fish & Richardson

[57] ABSTRACT

Disclosed are a conductive thienyl derivative monomolecular film covalently bonded to a substrate surface and method of manufacturing the same, and a silicon compound comprising 3-thienyl groups (thiophene derivative) used for forming the conductive monomolecular film and a method of manufacturing the same. A monomolecular ultrathin film comprising 3-thienyl groups and silicon groups is formed in the invention. The silicon compound used for forming the film is provided by reacting ω-(3-thienyl)-1-alkene compound to a monosilane derivative compound, in which three out of four hydrogen atoms of monosilane are replaced with halogen or alkoxy groups, in the presence of a transition metal catalyst. A substrate is dipped and held in a nonaqueous solution of the above-noted compound, thus chemically bonding the monomolecular film to the substrate surface. Furthermore, a thienyl derivative ultrathin film is formed by the electrolytic or catalytic polymerization of the monomolecular film.

4 Claims, 3 Drawing Sheets

CHEMICALLY ADSORBED ULTRATHIN FILM AND ITS MATERIAL, AND METHOD OF MANUFACTURING THE SAME

This application is a continuation of U.S. application Ser. No. 08/107,004, filed Aug. 17, 1993, now abandoned.

FIELD OF THE INVENTION

This invention relates to a new material—a silicon compound comprising 3-thienyl groups—and a method of manufacturing the same, a silicon polythienyl derivative ultrathin film and a method of manufacturing the same.

BACKGROUND OF THE INVENTION

It has been known that a conductive polythienyl can be formed by the electrolytic polymerization of a thienyl derivative. This conductive polythienyl has been applied to electronic devices such as diodes and field effect transistors, and to optoelectronic devices including electrochromic elements, optical memory elements and the like. Due to the recent miniaturization of devices, conductive films are consequently required to be made thinner. It has also been a goal to develop a thienyl derivative which can form a conductive ultrathin film much more easily and consistently than other materials.

Forming a conductive ultrathin film on a substrate surface by using a thienyl derivative can be done by the following procedure:
  providing a monomer by bonding long-chain organic groups to thienyl;
  forming a monomer monomolecular film on a substrate surface by the Langmuir-Blodgett method (LB method); and
  polymerizing the film on the substrate surface.

However, in case of this conventional thienyl derivative, the monomolecular film is only physically adsorbed to the substrate even by the LB method. The monomer is also likely to be evaporated or scattered before or during the polymerization process. Therefore, it has been difficult to form a fully optimal conductive ultrathin film.

SUMMARY OF THE INVENTION

In order to solve the above-noted problems, the objectives of this invention are to provide a new silicon compound comprising 3-thienyl groups—a thienyl derivative which can easily and firmly form an adsorbed monomolecular film on a substrate surface—and a method of manufacturing the same; to form a chemically adsorbed ultrathin film comprising the silicon compound mentioned above and a method of manufacturing the same; and to form a polythienyl derivative ultrathin film by using the chemically adsorbed ultrathin film and a method of manufacturing the same.

The new chemical compound of the invention is a silicon compound comprising 3-thienyl groups of Formula A:
Formula A

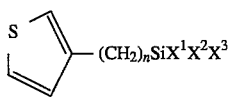

(wherein $X^1$, $X^2$ and $X^3$ can be the same or different and represent a halogen atom or an alkoxy group with 1–4 carbon atoms; n represents an integer from 6 to 30).

The method of manufacturing these silicon compounds comprising 3-thienyl groups comprises reacting an ω-(3-thienyl)-1-alkene of Formula B to a silicon hydride compound of Formula 3 in the presence of a transition metal catalyst.
Formula B

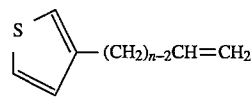

(wherein n represents an integer from 6 to 30)
Formula C

(wherein $X^1$, $X^2$ and $X^3$ are the same or different and represent a halogen atom or an alkoxy group with 1–4 carbon atoms).

The alkyl group shown in Formula A is a straight chain, comprising 6–30 carbon atoms. In forming a chemically adsorbed ultrathin film (monomolecular film) on a substrate surface, molecular chains are likely to become intertwined when there are more than 30 carbon atoms in the alkyl group. It is not preferable to have intertwined molecular chains, which prevent the formation of a film with the required precision. In a case that there are less than 6 carbon atoms in the alkyl group, the interaction among the carbon chains becomes small; as a result, a chemically adsorbed ultrathin film (monomolecular film) cannot be formed. The number of carbon atoms of the alkoxy groups is 1–4. The halogen can preferably be either chlorine or bromine.

A chemically adsorbed ultrathin film of the invention comprises 3-thienyl groups and silicon groups of the following Formula D:
Formula D

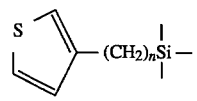

(wherein n represents an integer from 6 to 30)

It is preferable that the thienyl groups of this chemically adsorbed ultrathin film comprising 3-thienyl groups and silicon groups are treated with ring-opening polymerization.

The method of manufacturing a chemically adsorbed ultrathin film of the invention comprises contacting the chemical compound of Formula A to active hydrogen groups on a substrate surface in a liquid- or gaseous-phase atmosphere, thus generating a dehydrochlorination or alcohol elimination reaction and forming a chemically adsorbed ultrathin film comprising 3-thienyl groups and silicon groups on the substrate surface.

It is preferable that this method includes the electrolytic polymerization process of dipping and holding the chemically adsorbed ultrathin film in an electrolytic solution after forming the chemically adsorbed ultrathin film.

The Si—X groups of the silicon compound comprising 3-thienyl groups of the invention are reacted to hydroxy groups on the substrate surface. Alternatively, hydrolysis is generated due to the contact of the Si—X groups to the hydroxy groups. As a result, covalent bonds such as siloxane bonds are created at the substrate surface, and the compound is chemically adsorbed to the surface. Since the chemically adsorbed ultrathin film (monomolecular film) formed by the compound of this invention is firmly chemically bonded to the surface via covalent bonds, the film can keep its strength and uniform thickness without evaporating or scattering the compound. The thickness of the film can be at the angstrom or nanometer level.

A conductive ultrathin film formed by the electrolytic polymerization of 3-thienyl groups of the silicon compound of this invention can be applied to microelectronic or microoptoelectronic devices.

DETAILED DESCRIPTION OF THE INVENTION

EXAMPLES

Figure 1:
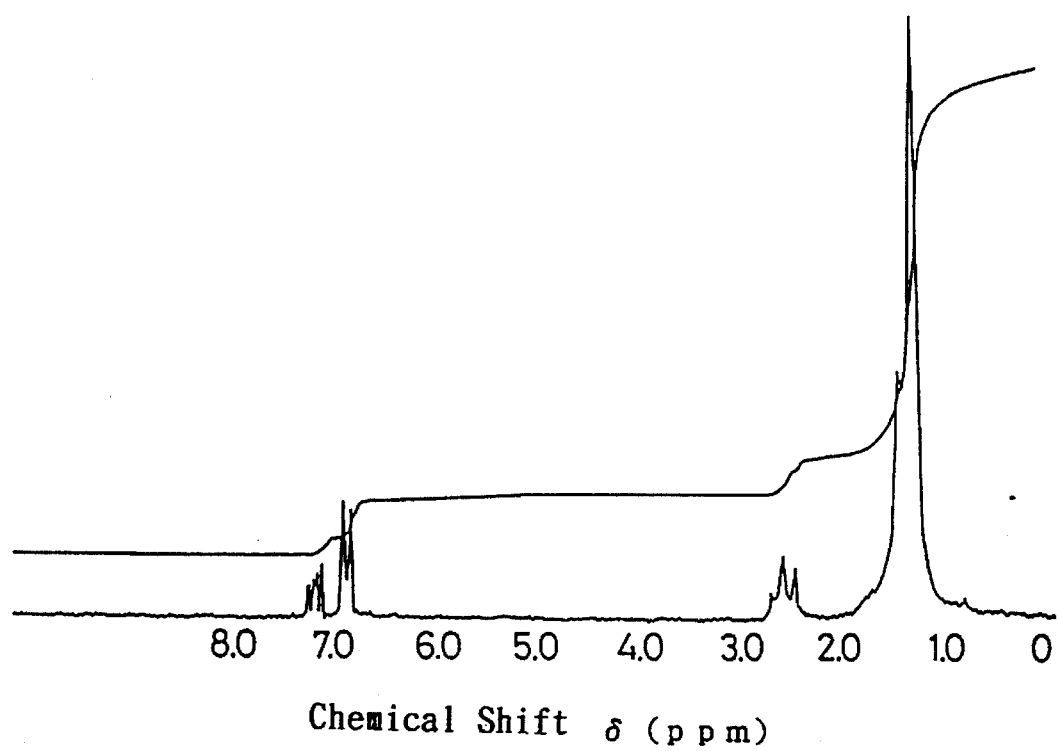
FIG. 1 is a graph showing the nuclear magnetic resonance spectrum of 10-(3-thienyl)-decyltrichlorosilane.

The invention is specifically described by referring to the following examples.

The examples of new chemical compounds of the invention are as follows:

ω-(3-thienyl)-alkyl-trihalogenosilane;

Si-[ω-(3-thienyl)-alkyl]-alkoxy-dihalogenosilane;

Si-[ω-(3-thienyl)-alkyl]-dialkoxy-halogenosilane; and

Si-[ω-(3-thienyl)-alkyl]-trialkoxysilane.

More specifically, the chemical compounds which can be used in the invention are as follows:

Formula 4: ω-(3-thienyl)-octyl-trichlorosilane

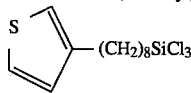

Formula 5: ω-(3-thienyl)-decyl-trichlorosilane

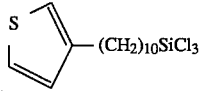

Formula 6: ω-(3-thienyl)-tetradecyl-trichlorosilane

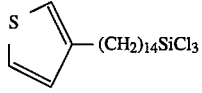

Formula 7: Si-(ω-(3-thienyl)-decyl)-trimethoxysilane

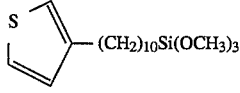

Formula 8: Si-(ω-(3-thienyl)-tetradecyl)-dimethoxy-monochlorosilane

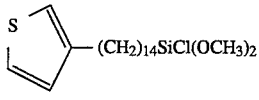

The compounds mentioned above can be produced by reacting silicon hydride compounds with ω-(3-thienyl)-1-alkene compounds.

As shown in the following Formulas 9–12, these ω-(3-thienyl)-1-alkene compounds are compounds in which 3-thienyl groups are bonded to the end of straight-chain 1-alkene comprising 6–30 carbon atoms. These compounds can be easily synthesized from 3-bromothiophene by the method of M. Kumada (Org. Syn., Col. 1, Vol. 6407 (1988)).

Formula 9: ω-(3-thienyl)-1-decene

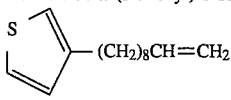

Formula 10: ω-(3-thienyl)-1-dodecene

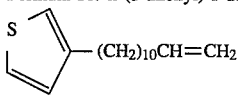

Formula 11: ω-(3-thienyl)-1-hexadecene

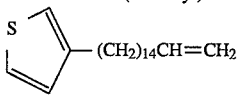

Formula 12: ω-(3-thienyl)-1-docosene

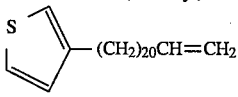

These silicon hydride compounds are monosilane derivative compounds in which three out of four hydrogen atoms of monosilane are replaced with halogen or alkoxy groups. The halogen is chlorine, bromine or the like. A methoxy group, an ethoxy group or the like is included as an alkoxy group.

The monosilane derivative compounds mentioned above can include the following:

trichlorosilane ($HSiCl_3$);

tribromosilane ($HSiBr_3$);

trimethoxysilane ($HSi(OCH_3)_3$);

triethoxysilane ($HSi(OCH_2CH_3)_3$); and dimethoxychlorosilane ($HSiCl(OCH_3)_2$).

In reacting the silicon hydride compounds to the above-mentioned ω-(1-pyrolyl)-1-alkene compounds, transition metal catalysts are used.

More specifically, the transition metal catalysts mentioned above are as follows:

hydrogenhexachloroplatinate ($H_2PtCl_6$);

dichlorobis(triphenylphosphine)platinate(II) ($[PtCl_2(PPh_3)_2]$);

dichlorobis(triphenylphosphine)palladium(II) ($[PdCl_2(PPh_3)_2]$); and chlorotris(triphenylphosphine)rhodium(I) ($[RhCl(PPh_3)_3]$).

Either one or a mix of the transition metal catalysts can be used in the invention.

The quantity of the catalyst needed for the reaction is suitably 10–500 ppm relative to that of the ω-(3-thiethyl)-1-alkene compound.

A reactor equipped with an agitator, thermometer, reflux condenser and dropping funnel can be used for the reaction described above. The reaction temperature is 20°–150° C., and the silicon hydride compound is dropped from the funnel onto the ω(3-thienyl)-1-alkene compound in the reactor. As reaction solvents, aprotic solvents including toluene, xylene, tetrahydrofuran (THF) or the like can be used.

Through a distillation procedure under reduced pressure after the reaction, a highly pure ω-(3-thienyl)-alkylsilane compound is generated. The obtained compound can be observed by mass spectrum, nuclear magnetic resonance spectrum, infrared absorption spectrum or like techniques.

A chemically adsorbed ultrathin film (monomolecular film) is formed on a substrate surface by using the above-noted silicon compound comprising 3-thienyl groups (chemical adsorbent) by the following procedure;

preparing a substrate 1 (FIG. 3) which has—or is given—active hydrogens such as hydroxyl groups (—OH), carboxyl groups (—COOH), amino groups (—NH$_2$), imino groups (>NH) or the like on its surface;

preparing a solution by dissolving the chemical adsorbent mentioned above in a nonaqueous organic solvent such as hexane, chloroform, carbon tetrachloride or the like; and dipping and holding the substrate in the prepared solution;

or alternatively, coating the solution on the substrate surface by a spray or roller.

Figure 3:
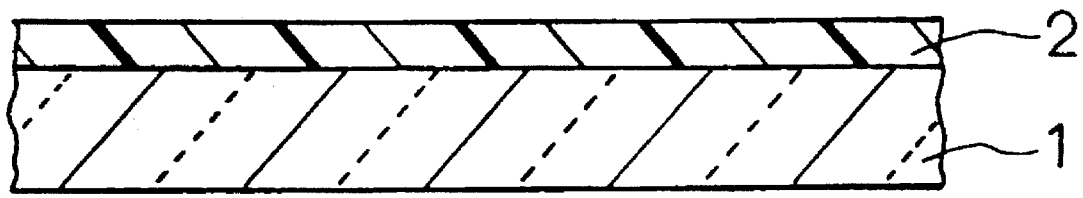
FIG. 3 is a schematic illustration of a chemically adsorbed ultrathin film (monomolecular film) of Example 2.

As a result, the chemical adsorbent is covalently bonded to the substrate surface by a dehydrohalogenation or alcohol elimination reaction between the active hydrogens on the substrate surface and the functional groups (halogenosilyl or alkoxysilyl groups) of the chemical adsorbent. After the reaction, the substrate is washed with a nonaqueous organic solution such as chloroform, thus removing unreacted chemical adsorbent. The substrate is then washed with water, and is dried at room temperature or under heat. As a result, a chemically adsorbed ultrathin film (monomolecular film) of a silicon compound comprising 3-thienyl groups is adhered to the substrate surface (FIG. 3). The thickness of the monomolecular film can be adjusted by changing the number of carbon atoms contained in the alkyl groups of ω-(3-thienyl)-alkylsilane compound.

Furthermore, a conductive ultrathin film can be formed by the electrolytic or catalytic polymerization of the abovementioned chemically adsorbed ultrathin film (monomolecular film).

Figure 4:
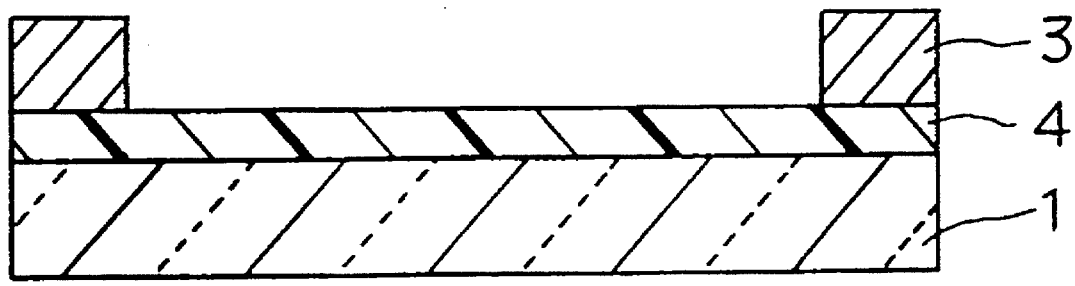
FIG. 4 is a schematic illustration of a polythienyl derivative ultrathin film of Example 3.

A polythienyl derivative ultrathin film was formed on a substrate surface by the following procedure:

depositing platinum 3 onto a section of the ultrathin film surface, thus preparing a working electrode (FIG. 4);

preparing an acetonitrile solution, containing lithium perchlorate anhydride (tetraethylammoniumtetrafluoroborate, tetrabutylammoniumperchlorate or the like) at a concentration of 0.05 mol/l, as a supporting electrolyte;

dipping and holding substrate 1 formed with chemically adsorbed ultrathin film 2, along with a gold counter electrode and a NaCl-calomel reference electrode, in the prepared solution; and polymerizing substrate 1 with 100 V per second scanning speed and 150 μA/cm$^2$ current density in an inert gas (such as helium gas) atmosphere, thereby forming a polythienyl derivative ultrathin film 4 on substrate 1 (FIG. 4).

The formation of polythienyl derivative ultrathin film 4 was proved by analysis with a Fourier transform infrared absorption spectrochemical instrument.

Example 1

Prepared 10-(3-thienyl)-1-decene was reacted to trichlorosilane, thus synthesizing 10-(3-thienyl)decyltrichlorosilane.

As a step of preparing the 10-(3-thienyl)-1-decene, Grignard reagent was produced by the following procedure:

placing 4.28g (0.176 mol) magnesium and 88 ml ether in a 200 ml flask, equipped with an agitator, reflux condenser, thermometer and dropping funnel; and dropping 38.6 g (0.176 mol) 10-bromo-1-decene from the funnel into the flask at 40°–50° C. and reacting 10-bromo-1-decene with the magnesium, thus preparing Grignard reagent (10-bromomagnesium-1-decene).

Moreover, 25.6 g (0.157 mol) 3-bromothiophene; 0.078 g (0.145 mmol) nickel chloride. 1, 1, 5, 5-tetraphenyl-1, 5, phosphapentane [NiCl$_2$((C$_6$H$_5$)$_2$PCH$_2$CH$_2$CH$_2$P(C$_6$H$_5$)$_2$)]; and 160 ml ether were placed in a 500 ml flask, equipped with an agitator, reflux condenser, thermometer and dropping funnel. The Grignard reagent prepared in the above-mentioned procedure was dropped from the funnel into the flask at 0°–5° C., thus providing 10-(3-thienyl)-1-decene solution by a Grignard reaction.

Furthermore, the 10-(3-thienyl)-1-decene solution was purified by the following process:

adding 100 ml water to the solution, thus separating an organic layer from the solution;

removing solvent from the organic layer;

distilling the organic layer at a 115°–117° distillation point and 2 mmHg distillation pressure, thereby providing 23.6 g of purified 10-(3-thienyl)-1-decene.

Then, 10-(3-thienyl)-decyltrichlorosilane was synthesized from 10-(3-thienyl)-1-decene by the following process:

placing 22.2 g (0.100 mol) 10-(3-thienyl)-1-decene and 0.1 g isopropylalcohol solution, containing hydrogenhexachloroplantinate(IV)hydrate (H$_2$PtCl$_6$.6H$_2$O) at a concentration of 4%, in a 100 ml flask, equipped with an agitator, reflux condenser, thermometer and dropping funnel, thus preparing a solution;

dropping 16.3 g (0.120 mol) trichlorosilane from the funnel to the solution for one hour at 60°–70° C.; and aging the solution for two hours at 70° C.

The solution was then distilled at a 124°–127° C. distillation point and 0.15 mmHg distillation pressure, thus providing 22.0 g of purified 10-(3-thienyl)-decyltrichlorosilane. The yield was 61.5%.

The results of mass spectrum (MS), nuclear magnetic resonance spectrum (NMR) and infrared absorption spectrum (IR) of the compound, 10-(3-thienyl)-decyltrichlorosilane, are shown below.

Mass Spectrum (MS): m/z (Assignment) 356, 358, 360 (Molecular Ion Peak) 133, 135, 137 (SiCl$_3$) 98(M-C$_3$H$_{17}$SiCl$_3$)

Nuclear Magnetic Resonance Spectrum (NMR): δ (ppm) (See FIG. 1)

Figure 2:
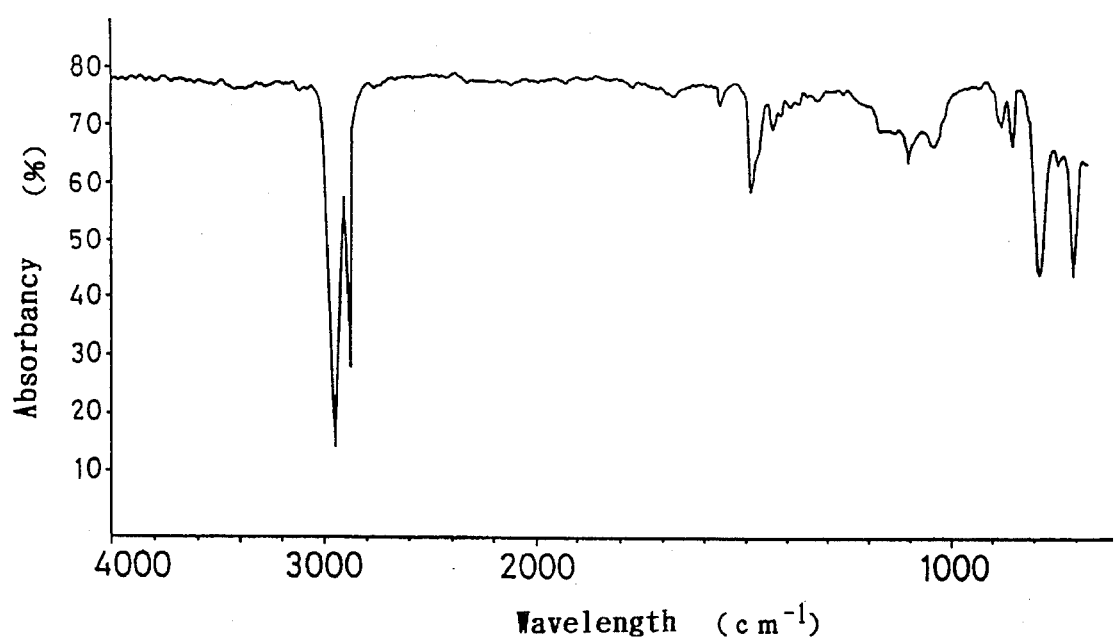
FIG. 2 is a graph showing the infrared absorption spectrum of 10-(3-thienyl)-decyltrichlorosilane.

Infrared Absorption Spectrum (IR): cm$^{-1}$ (See FIG. 2)

According to the results, the compound was proved to be 10-(3-thienyl)-decyltrichlorosilane.

Example 2

A chemically adsorbed ultrathin film formed by using the silicon compound comprising 3-thienyl groups and method of manufacturing the same are explained below by referring to FIG. 3.

The method of manufacturing the ultrathin film is as follows:

dissolving 10 mg 10-(3-thienyl)-decyltrichlorosilane in 100 ml mixed solvent of 80% by weight of n-hexadecane (toluene, xylene, hexane or the like), 12% by weight of carbon tetrachloride and 8% by weight of chloroform, thus preparing a solution;

washing a substrate such as a quartz substrate 1 of FIG. 3 (or metallic plate, quartz plate, ceramic substrate, molded plastic substrate, etc.) with an organic solvent or water;

drying substrate 1;

dipping and holding substrate 1 in the prepared solution for one hour (wherein the time for dipping and holding substrates varies depending on the type of substrates and the surface roughness of the substrates);

reacting the hydroxyl groups on the substrate surface to the SiCl group of the above-noted 10-(3-thienyl)-decyltrichlorosilane, thereby generating a dehydrochlorination reaction as shown in Formula 13;

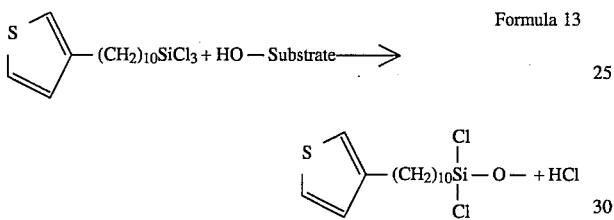

Formula 13 washing and removing unreacted 10-(3-thienyl)-decyltrichlorosilane with a nonaqueous solvent such as Freon-113;

reacting substrate 1 with water, thus hydrolyzing the chlorosilyl groups to silanol groups as shown in Formula 14; and

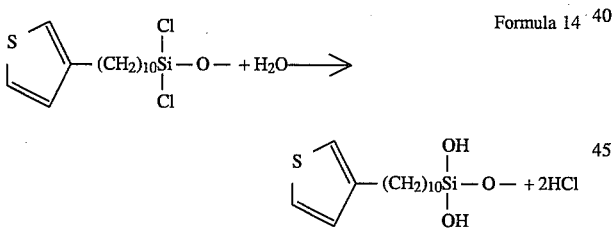

Formula 14 drying substrate 1, thereby dehydrating and crosslinking the silanol groups and forming siloxane bonds and a chemically adsorbed ultrathin film (monomolecular film) as shown in Formula 15.

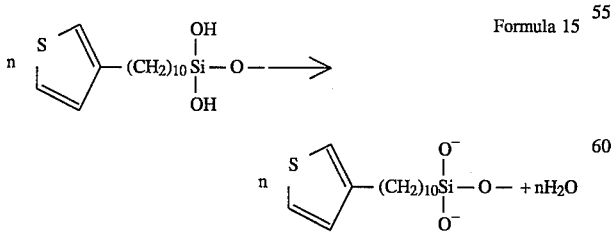

Formula 15

By following the above-noted procedures, a chemically adsorbed ultrathin film (monomolecular film) 2 comprised of 10-(3-thienyl)-decylsilanol was chemically bonded to the surface of substrate 1 (FIG. 3). The thickness of the film was about 2.5 nm.

Moreover, quartz substrate 1 formed with chemically adsorbed ultrathin film (monomolecular film) 2 was dipped and held in 300 ml ether solution, containing ferric chloride anhydride at a concentration of 0.12 mol/l. The formation of the monomolecular film was confirmed by analysis with a Fourier transform infrared absorption spectrochemical instrument.

Example 3

A polythienyl derivative ultrathin film, formed by polymerizing the above-noted ultrathin film, and method of manufacturing the same are explained by referring to FIG. 4.

A polythienyl derivative ultrathin film 4 was formed on a substrate surface by the following procedure:

depositing platinum 3 to a sectional surface of chemically adsorbed ultrathin film 2, thus preparing a working electrode;

preparing an acetonitrile solution, containing lithium perchlorate anhydride (tetraethylammoniumtetrafluoroborate, tetrabutylammoniumperchlorate or the like) at a concentration of 0.05 mol/l, as a supporting electrolyte;

dipping and holding substrate 1 formed with chemically adsorbed ultrathin film 2, along with a gold counter electrode and a NaCl-calomel reference electrode, in the prepared solution; and polymerizing substrate 1 with 100 V per second scanning speed and 150 μA/cm² current density in an inert gas (such as helium gas) atmosphere.

The formation of polythienyl derivative ultrathin film 4 was proved by a Fourier transform infrared absorption spectrochemical instrument for analysis.

As mentioned above, in applying a silicon compound comprising 3-thienyl groups of the invention and method of manufacturing the same, a thienyl derivative ultrathin film can be formed firmly on a substrate surface. The conductive ultrathin film, moreover, can be easily formed by the electrolytic or catalytic polymerization of the chemically adsorbed ultrathin film (monomolecular film).

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes which come within the meaning and range of equivalency of the claims are intended to be embraced therein.

We claim;

1. A 3-thienyl-alkyl-silane compound represented by Formula A:

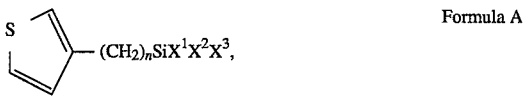

Formula A wherein $X^1$, $X^2$ and $X^3$ are the same or different and each represents a halogen atom or an alkoxy group with 1–4 carbon atoms; and n represents an integer from 6 to 30.

2. A 3-thienyl-alkyl-silane derived, chemically adsorbed ultrathin film represented by Formula D:

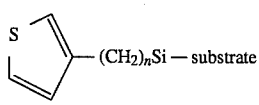

Formula D wherein the substrate comprises an oxygen atom or nitrogen atom and the point of attachment to the silicon atom in Formula D is with an oxygen atom or nitrogen atom; and n represents an integer from 6 to 30.

3. The chemically adsorbed ultrathin film, of claim 2 wherein the thienyl groups of Formula D are treated with ring-opening polymerization.

4. The 3-thienyl-alkyl-silane compound as in claim 1, wherein the halogen atom is selected from the group consisting of chlorine or bromine.

* * * * *